(12) United States Patent
Dankelman et al.

(10) Patent No.: US 8,435,260 B2
(45) Date of Patent: May 7, 2013

(54) SURGICAL INSTRUMENT

(75) Inventors: Jennigje Dankelman, Delft (NL); Tim Horeman, Delft (NL)

(73) Assignee: Technische Universiteit Delft, Delft (NL)

( * ) Notice: Subject to any disclaimer, the term of this patent is extended or adjusted under 35 U.S.C. 154(b) by 253 days.

(21) Appl. No.: 12/689,808

(22) Filed: Jan. 19, 2010

(65) Prior Publication Data

US 2010/0174244 A1 Jul. 8, 2010

Related U.S. Application Data

(63) Continuation of application No. PCT/NL2008/050409, filed on Jun. 20, 2008.

(30) Foreign Application Priority Data

Jul. 19, 2007 (NL) ..................................... 2000763

(51) Int. Cl.
*A61B 17/34* (2006.01)
(52) U.S. Cl.
USPC .......................................... 606/185; 604/264

(58) Field of Classification Search .................. 606/108, 606/184, 185; 604/164, 264
See application file for complete search history.

(56) References Cited

U.S. PATENT DOCUMENTS

| | | | |
|---|---|---|---|
| 5,549,563 A * | 8/1996 | Kronner | ................... 604/170.03 |
| 2002/0038077 A1 | 3/2002 | de al Torre et al. | |
| 2002/0099402 A1 | 7/2002 | Buckman et al. | |
| 2005/0054894 A1 | 3/2005 | Aizenfeld et al. | |
| 2007/0112336 A1 | 5/2007 | Aizenfeld et al. | |

FOREIGN PATENT DOCUMENTS

| | | |
|---|---|---|
| EP | 0537768 | 4/1993 |
| WO | WO-9204932 | 4/1992 |
| WO | WO-9704828 | 2/1997 |
| WO | WO-2006072936 | 7/2006 |
| WO | WO-2007057880 | 5/2007 |

* cited by examiner

*Primary Examiner* — Victor Nguyen
(74) *Attorney, Agent, or Firm* — Jeffrey D. Myers; Samantha A. Updegraff; Peacock Myers, P.C.

(57) ABSTRACT

A surgical instrument for minimally invasive surgery, having a handle, a shaft and an actuating part, as well as a gastight cover surrounding the shaft, wherein the cover is provided with a coupler that has a feed-through opening with a lockable seal, through which feed-through opening, after the seal is unlocked, the shaft with the actuating part can reach.

4 Claims, 4 Drawing Sheets

SURGICAL INSTRUMENT

CROSS-REFERENCE TO RELATED APPLICATIONS

This application is a continuation application of International Patent Cooperation Treaty (PCT) Application Ser. No. PCT/NL2008/050409, entitled "Surgical Instrument", to Technische Universiteit Delft, filed on Jun. 20, 2008, which is a continuation application of Netherlands Patent Application Ser. No. NL 2000763, to Technische Universiteit Delft, filed on Jul. 19, 2007, and the specifications and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention

The invention relates to a surgical instrument for minimally-invasive surgery, comprising a handle, a shaft and an actuating part at the end of the shaft farthest away from the handle. The invention also relates to a trocar or cannula that is provided with an isolator to be placed on a patient to safeguard a sterile environment 2. Description of Related Art The literature relating to the provision of a sterile surgical environment by using isolator means is extensive.

In the British Medical Journal 1, 1974, pp 322-324 J. McLauchlan et al. describe in an article "The Surgical Isolator", the use of a plastic cover placed under pressure and enveloping the patient. Surgery takes place through access openings provided in the cover.

A similar isolator is also known from Stephen N. Joffe et al., '[x]A Closed System Surgical Isolator for Major Elective Abdominal Operations', World Journal of Surgery, Vol. 2, Nr. 1, January 1978, pp. 123-130.

The patent literature is similarly extensive; the isolators known from the various patent publications generally relate to use in conventional surgery. The publications include the European patent application EP-A-537768, the American patent publications numbers U.S. Pat. Nos. 2,403,400, 2,473,033, 1,118,657, 4,026,286, 5,083,558, 5,316,541, 5,728,041, 6,321,764, 1,488,772 and the published American patent applications 2004/0074212, 2004/024014, 2004/0116770 and 2007/0112336.

For some time now the aim has been to reduce the number of major surgical operations by performing minimally invasive surgery instead. So far, the same standards of working conditions regarding the preservation of a sterile working environment apply as for conventional surgery.

BRIEF SUMMARY OF THE INVENTION

The present invention is based on the view that with minimally invasive surgery the requirements concerning the guarantee of a sterile working environment may be less stringent, and that it suffices that the sterile working environment is guaranteed at the place on the patient where the minimally invasive surgical operation takes place.

DESCRIPTION OF THE INVENTION

The object of the invention is to increase the flexibility of the minimally invasive surgery, in particular by ensuring that during the exchange of surgical instruments the sterile working environment is guaranteed.

To this end a surgical instrument, as well as a trocar or an assembly of these two is proposed in accordance with the invention, as characterized by one or several of the appended claims.

DETAILED DESCRIPTION OF THE INVENTION

In a first aspect of the invention, the surgical instrument is characterized by a gastight cover surrounding the shaft, wherein the cover is provided with a coupler that has a feed-through opening with a lockable seal through which feed-through opening, after the seal is unlocked, the shaft with the actuating part can reach.

When this surgical instrument is not coupled with the trocar, the gastight cover with the lockable seal ensures that the part of the instrument that can be introduced into the patient, namely the shaft and the actuating part, remains sterile. It is desirable that the lockable seal can be unlocked by coupling the coupler with a coupling member of a trocar and that in the absence of this coupling, the seal is locked. Correspondingly, a trocar is proposed in accordance with the invention, which is provided with an isolator to be placed on a patient to guarantee a sterile environment, and which trocar has a coupling member designed to cooperate with the coupler of the above-mentioned surgical instrument so as to unlock the seal of the coupler only when the coupling between the coupling member and the coupler is in effect.

The assembly of the surgical instrument and the trocar according to the invention is preferably embodied such that the coupler and the coupling member are provided with features for realizing a detachable snap connection.

A very suitable embodiment of this is characterized in that the features for the detachable snap connection comprise at least one leaf spring with a projection, and a receiving space for receiving this at least one leaf spring, which receiving space comprises a rim behind which the projection can catch, wherein the leaf spring and the receiving space are received in respectively the coupler and the coupling member or vice versa. A preferred embodiment of the surgical instrument entails that the coupler comprises a locking pin operable by the coupling member of the trocar, which has a locking position and a release position, and that in the locking position the seal is locked and in the release position the feed-through opening is open to allow the shaft to pass through. The same is further preferably characterized in that the locking pin cooperates with a movable plate within the coupler, which comprises the feed-through opening for the shaft and into which feed-through opening a shearing pin can be inserted such that, when in the locking position, the plate is fixed and the shearing pin prevents the shaft from passing through, and in that in the release position the shearing pin opens the feed-through opening to allow the shaft to pass through.

To promote the ability of maintaining a sterile environment for the relevant surgical instrument as much as possible, it is desirable that the preferential position of the locking pin is the locking position.

The ease of use of the surgical instrument according to the invention benefits by the movable plate being spring loaded such that when the locking pin is put into the release position, the plate moves to a position in which the shearing pin opens the feed-through opening.

The trocar according to the invention is provided with an isolator for placing on a patient over the surgery site, to guarantee a sterile environment. To provide a simple manner for keeping the trocar itself sterile before its introduction into the patient, the trocar according to the invention is characterized in that the isolator, prior to its first use, is a closed balloon surrounding the trocar. Placing the trocar with the balloon on the patient and subsequently introducing the trocar causes the balloon to be pierced, with the trocar being immediately ready to be used for introducing a surgical instrument.

As already mentioned above, the seal through which the shaft with the actuating part of the surgical instrument can reach, will only open as a result of cooperation between the trocar and the surgical instrument.

The detachable snap connection provided between the coupler of the surgical instrument and the coupling member of the trocar ensures that the above-mentioned unlocking of the seal can only take place after said snap connection is accomplished. The movable plate provided in the coupler of the surgical instrument and the at least one leaf spring of the detachable snap connection then cooperate such that in the release position, where the shearing pin opens the feed-through opening, the movable plate of the surgical instrument prevents movement of the at least one leaf spring and the projection remains caught behind the rim of the receiving space.

BRIEF DESCRIPTION OF THE SEVERAL VIEWS OF THE DRAWINGS

Hereinafter the invention will be explained in more detail by way of a schematic illustration of an exemplary embodiment of the surgical instrument, the trocar and the assembly thereof, as shown in the drawing.

It is particularly emphasized that the exemplary embodiment as shown with reference to the drawing places no limitation on the appended claims, but that the following explanation merely serves to elucidate possible ambiguities, without limiting the claims to anything shown in the drawing. The drawing shows in:

DETAILED DESCRIPTION OF THE INVENTION

Figure 1:
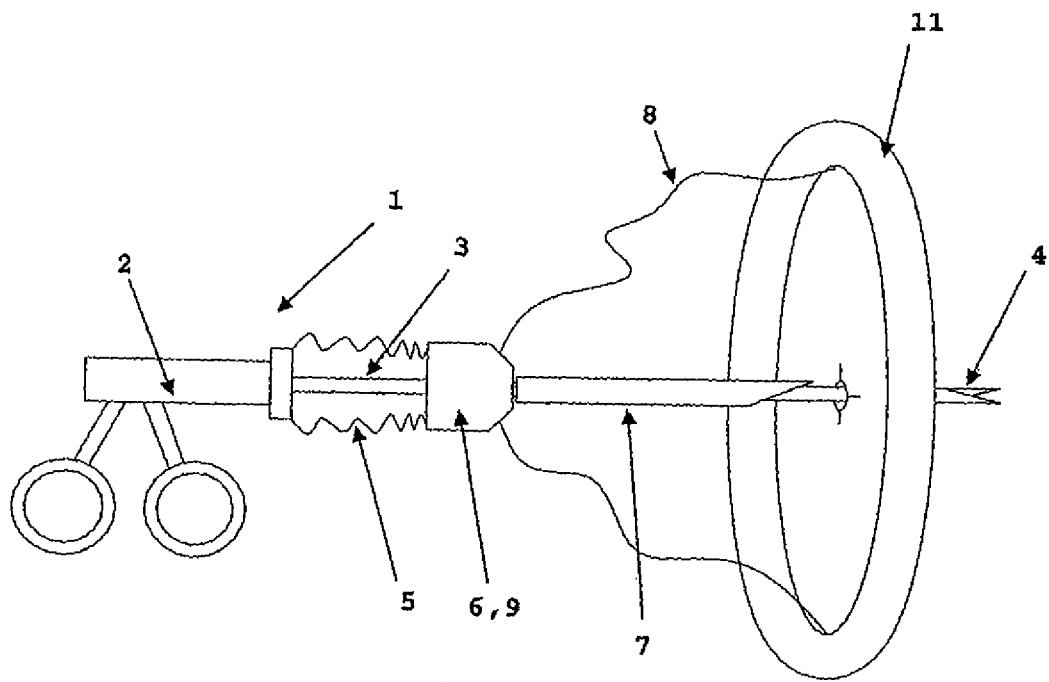
FIG. 1, an assembly of a trocar according to the invention in combination with a surgical instrument.

Like reference numerals in the figures refer to like components.

Figure 3:
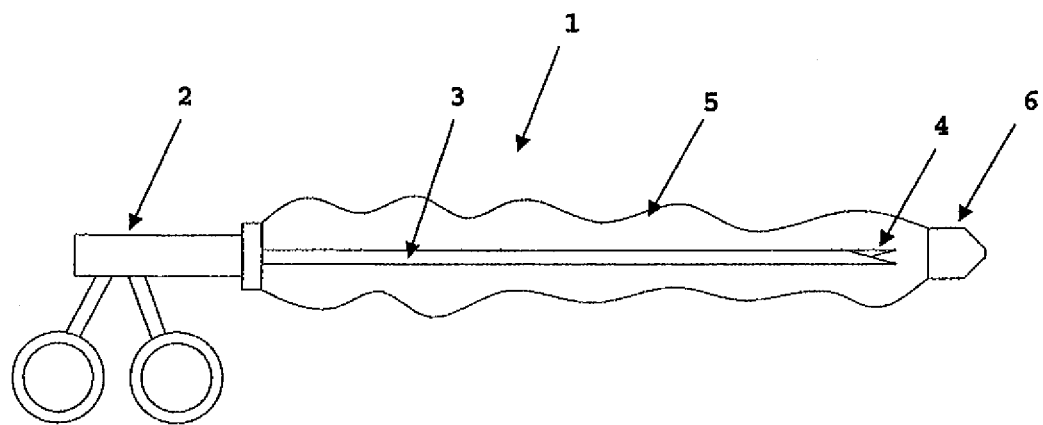
FIG. 3, a surgical instrument according to the invention.

FIG. 3 shows the surgical instrument 1 according to the invention, which is designed for minimally invasive surgery and which comprises a handle 2, a shaft 3 and an actuating part 4 at the end of the shaft 3 opposite to the handle 2.

Figure 4:
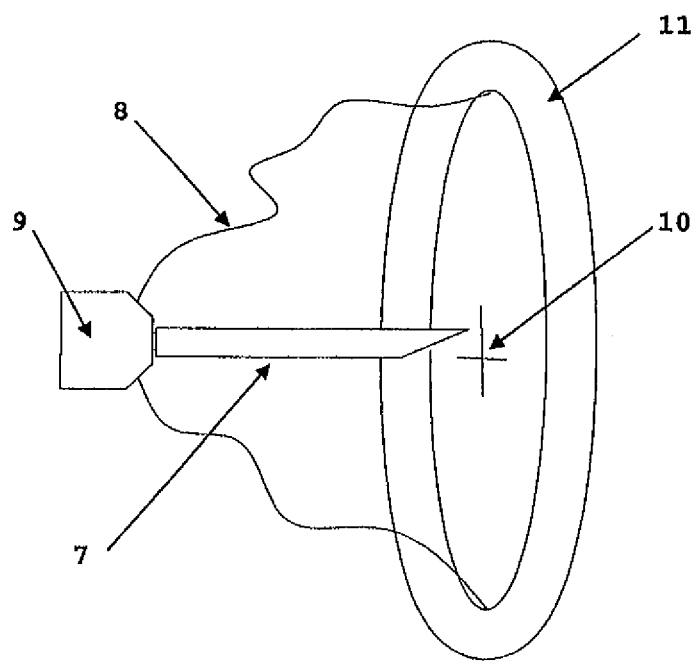
FIG. 4 a trocar with an integrated isolator according to the invention.

The surgical instrument 1 is further characterized by a gastight cover 5, provided with a coupler 6, comprising a feed-through opening with a lockable seal that will be described in more detail below. After unlocking the seal, this feed-through opening allows the shaft 3 with the actuating part 4 to pass through. FIG. 4 shows the trocar 7 according to the invention, provided with an isolator 8 that can be placed on a patient to guarantee a sterile environment. This trocar 7 has a coupling member 9, which is designed to cooperate with the coupler 6 of the surgical instrument 1 shown in FIG. 3 in such a way that when such a coupling is in effect, the above-mentioned seal of the coupler 6 is unlocked.

FIG. 4 further shows that the isolator 8 provides a closed space. The isolator 8 may be embodied as balloon, which when placed on the patient may be pierced, for example, at the cross 10. To stably place the balloon on the patient it may possibly be provided with a supporting rim 11.

Figure 2:
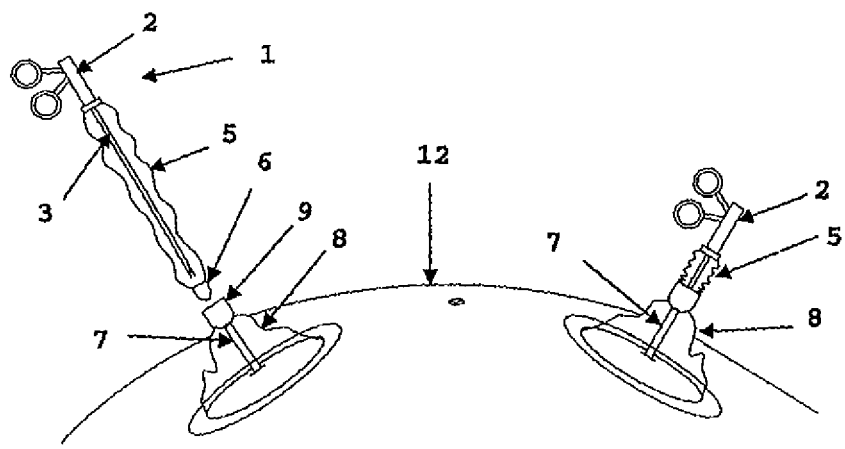
FIG. 2, two trocars and surgical instruments according to the invention, placed on the abdomen of a patient.

FIG. 1 shows the assembly of the trocar 7 and the surgical instrument 1 according to the invention, after a coupling has been realized between the coupler 6 of the surgical instrument 1 and the coupling member 9 of the trocar 7. This opens the seal of the coupler 6 and allows the shaft 3 to reach through this seal, through the trocar 7, and out of the isolator 8 of this trocar 7. The actuating part 4 is then completely inside the patient. In practice, the situation shown in FIG. 1 will occur when the assembly is in use during a minimally invasive operation as shown in FIG. 2 on the right. The actuating part is shown to be inside the abdominal cavity of the patient 12.

On the left of FIG. 2 a situation is shown, in which the surgical instrument 1 is uncoupled from the trocar 7. In this situation the shaft 3 and the actuating part 4 are completely inside the protection formed by the cover 5, while the application of a suitable overpressure in the abdominal cavity of the patient 12 prevents non-sterile air from entering the patient 12 via the coupling member 9 and the trocar 7.

Figure 5A:
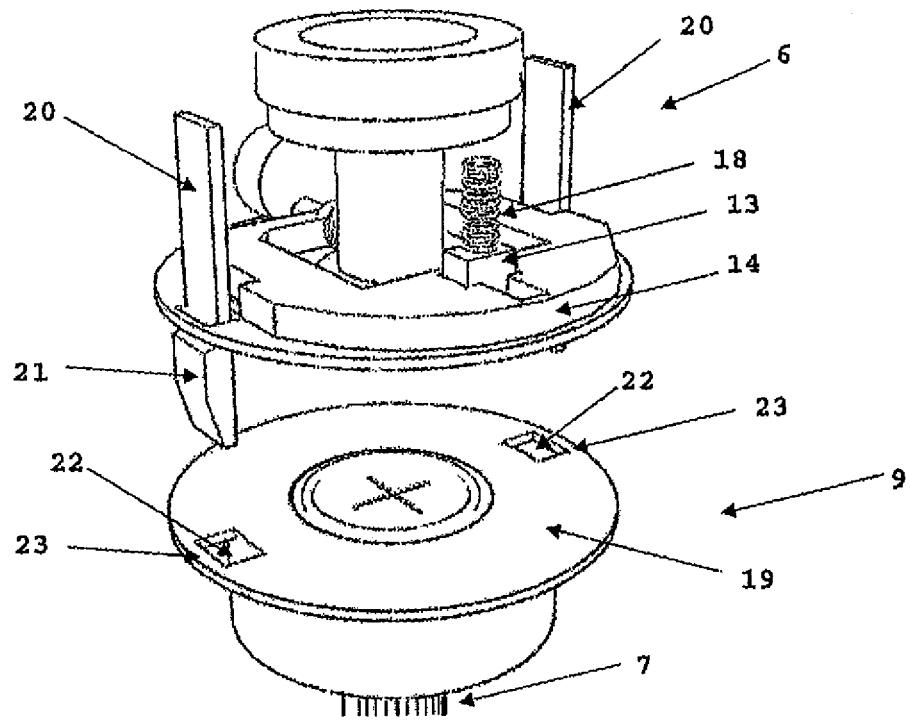
FIGS. 5a en 5b, in detail a coupling member and coupler of respectively trocar and surgical instrument in the uncoupled situation, and FIGS. 6a en 6b, in detail the coupling member and coupler shown in FIGS. 5a and 5b in the coupled situation.

FIGS. 5a/5b show in detail the coupler 6 of the surgical instrument and the coupling member 9 of the trocar 7, both with the omission of components that are not necessary for the explanation following below.

Figure 5B:
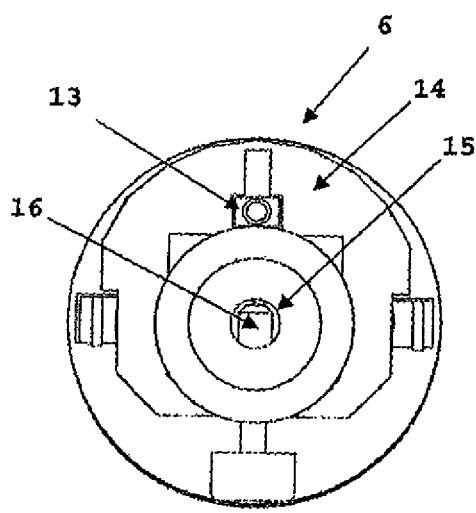

FIG. 5a shows a perspective view and FIG. 5b shows a top view of the coupler 6 in the situation where it is not connected with the coupling member 9 of the trocar 7.

Figure 6A:
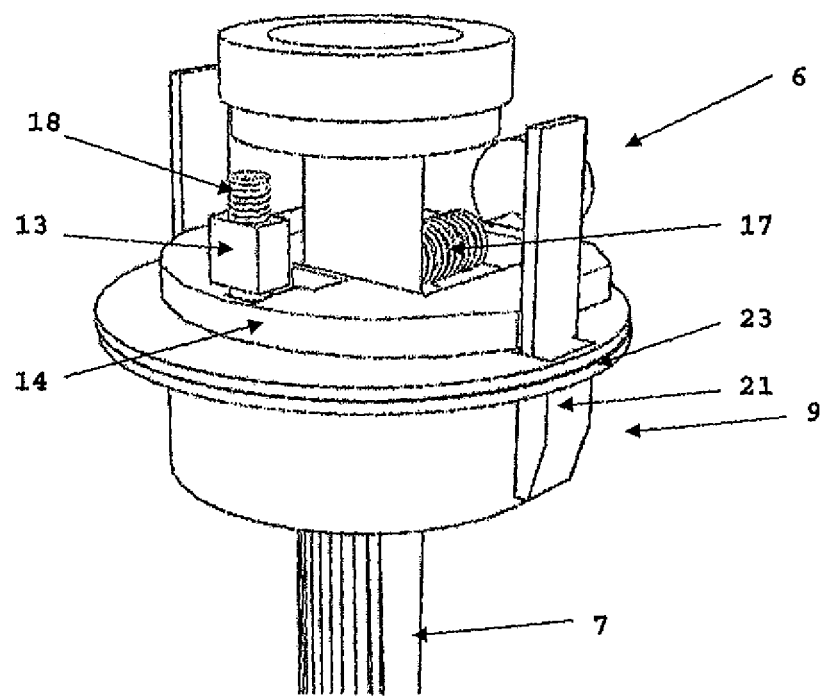
Figure 6B:
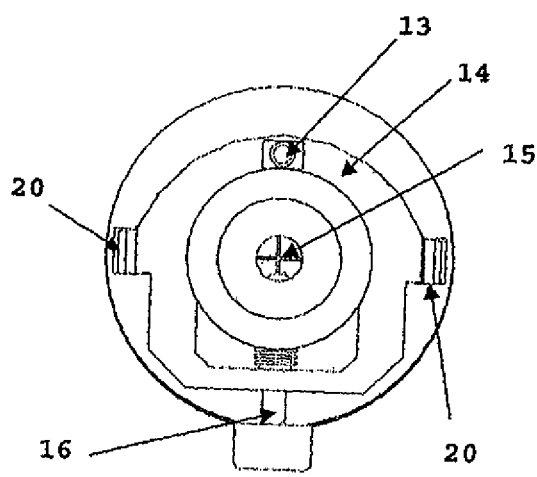

FIGS. 6a and 6b show the coupler 6 and the coupling member 9 of the surgical instrument and the trocar in the coupled situation in a perspective view and a top view, respectively. The coupler 6 of the surgical instrument comprises a locking pin 13 that can be moved upwards by coupling the coupler 6 of the surgical instrument with the coupling member 9 of the trocar 7. This moves the locking pin 13 from the locked position shown in FIG. 5a to the release position shown in FIG. 6a. This latter position allows a movable plate 14 comprised in the coupler 6 to be moved to a position in which a feed-through opening 15 for the shaft of the surgical instrument is opened. As shown in FIG. 5b and FIG. 6b, this feed-through opening 15 is provided in the movable plate 14. However, if the locking pin 13 is in the locking position shown in FIG. 5a and FIG. 5b, the movable plate 14 is moved to a position in which a shearing pin 16 locks the feed-through opening 15. FIG. 6b shows that when putting the locking pin 13 into the release position, the movable plate 14 is placed in a position in which the shearing pin 16 no longer locks this feed-through opening 15, thereby unlocking the respective lockable seal. The above-mentioned movement of the movable plate 14 that occurs when the locking pin 13 is in the release position, is preferably activated by spring loading. A spring serving this purpose is indicated with reference numeral 17. The locking pin 13 is similarly spring loaded with the aid of a spring 18, as a result of which the preferential position of the locking pin 13 is the locking position.

To operate the locking pin 13, the same rests on a supporting surface 19 of the coupling member 9 of the trocar 7; see FIG. 5a. In particular FIGS. 5a and 6a show that the coupler 6 of the surgical instrument and the coupling member 9 of the trocar 7 are provided with features for providing a detachable snap connection between them.

These features for the detachable snap connection involve two leaf springs 20, each provided with a projection 21, which leaf springs 20 are provided, for example, on the coupler 6. Each leaf spring 20 cooperates with a receiving space 22 provided in the coupling member 9 of the trocar 7, which space 22 serves for receiving the leaf spring 20 in such a way that the projection 21 of the leaf spring 20 catches behind a rim 23 of the receiving space 22. It will be obvious that the position of the leaf spring 20 and the receiving space 22 are also interchangeable.

FIG. 6a and FIG. 6b show the situation where the coupler 6 of the surgical instrument and the coupling member 9 of the trocar 7 are coupled. FIG. 6b clearly shows that when the movable plate 14 has assumed a position in which the feed-through opening 15 for the shaft 3 and the actuating part 4 of the surgical instrument 1 is open, said plate 14 simultaneously locks the leaf springs 20 in their position and thus prevents the catch contact between their projections 21 and the rim 23 of the receiving spaces 22 from being broken.

What is claimed is:

1. A surgical instrument for minimally-invasive surgery, comprising a handle, a shaft and an actuating part, characterized by a gastight cover surrounding the shaft, wherein the cover is provided with a coupler that has a feed-through opening with a lockable seal through which feed-through opening, after the seal is unlocked, the shaft with the actuating part can reach; wherein the lockable seal can be unlocked by coupling the coupler with a coupling member of a trocar and that in the absence of this coupling member, the seal is locked; wherein the coupler comprises a locking pin operable by the coupling member of the trocar, which has a locking position and a release position, and that in the locking position the seal is locked and in the release position the feed-through opening is open to allow the shaft to pass through.

2. The surgical instrument according to claim 1, wherein the locking pin cooperates with a movable plate within the coupler, which comprises the feed-through opening for the shaft and into which feed-through opening a shearing pin can be inserted such that, when in the locking position, the plate is fixed and the shearing pin prevents the shaft from passing through, and in that in the release position the shearing pin opens the feed-through opening to allow the shaft to pass through.

3. The surgical instrument according to claim 2, wherein the movable plate is spring loaded such that when the locking pin is put into the release position, the plate moves to a position in which the shearing pin opens the feed-through opening.

4. The surgical instrument according to claim 1, wherein the preferential position of the locking pin is the locking position.

* * * * *